United States Patent [19]

Wong

[11] 4,402,695

[45] * Sep. 6, 1983

[54] DEVICE FOR DELIVERING AGENT IN VAGINA

[75] Inventor: Patrick S. Wong, Hayward, Calif.

[73] Assignee: Alza Corporation, Palo Alto, Calif.

[*] Notice: The portion of the term of this patent subsequent to Sep. 1, 1998, has been disclaimed.

[21] Appl. No.: 249,005

[22] Filed: Mar. 30, 1981

Related U.S. Application Data

[60] Continuation-in-part of Ser. No. 113,499, Jan. 21, 1980, Pat. No. 4,286,587, which is a continuation-in-part of Ser. No. 950,454, Oct. 11, 1978, Pat. No. 4,215,691, which is a division of Ser. No. 775,718, Mar. 9, 1977, abandoned.

[51] Int. Cl.$^3$ .............................................. A61M 7/00
[52] U.S. Cl. .................................................... 604/892
[58] Field of Search ............................... 128/127–130, 128/260–261; 604/890–892

[56] References Cited

U.S. PATENT DOCUMENTS

| | | | |
|---|---|---|---|
| 3,545,439 | 12/1980 | Ducan ................................. | 128/260 |
| 3,920,805 | 11/1975 | Roseman ............................. | 424/15 |
| 3,948,254 | 4/1976 | Zaffaroni ........................... | 128/127 |
| 3,948,262 | 4/1976 | Zaffaroni ........................... | 128/260 |
| 3,995,634 | 12/1976 | Drobish .............................. | 128/260 |
| 4,215,691 | 8/1980 | Wong ................................. | 128/260 |
| 4,286,587 | 9/1981 | Wong ................................. | 128/127 |
| 4,292,965 | 10/1981 | Nash et al. ........................ | 128/127 |

Primary Examiner—C. Fred Rosenbaum
Attorney, Agent, or Firm—Paul L. Sabatine; Edward L. Mandell

[57] ABSTRACT

An intravaginal therapeutic system for the pre-programmed, unattended delivery of a drug is disclosed. The system comprises (a) a drug, (b) a delivery module comprising a reservoir for storing the drug in an amount for execution of the program, a rate controller which maintains the rate of drug delivered in a therapeutically effective amount throughout the life of the system, an energy source for transferring drug from the reservoir to the vagina, and a portal for releasing the drug from the module to the vagina, (c) a platform which integrates the module into a unit sized, shaped and adapted for insertion and retention in a vagina, and (d) therapeutic program which provides for the controlled release of drug to produce a beneficial effect over a prolonged period of time.

38 Claims, 4 Drawing Figures

DEVICE FOR DELIVERING AGENT IN VAGINA

CROSS-REFERENCE TO COPENDING APPLICATION

This patent application is a continuation-in-part of U.S. patent application Ser. No. 113,499, filed on Jan. 21, 1980, now U.S. Pat. No. 4,286,587 issued Sept. 1, 1981, which application is a continuation-in-part of U.S. patent application Ser. No. 950,454 filed on Oct. 11, 1978, now U.S. Pat. No. 4,215,691 issued on Aug. 5, 1980, which application is a division of U.S. patent application Ser. No. 775,718 filed on Mar. 9, 1977, and now abandoned. These applications are incorporated herein by reference, and benefit is claimed of their filing dates. These applications are assigned to the ALZA Corporation of Palo Alto, Calif.

FIELD OF THE INVENTION

This invention pertains to an intravaginal system. The system comprises a drug, a delivery module, a platform and a therapeutic program that operates as a unit for delivering an effective amount of drug to the vagina. More specifically, the invention relates to an intravaginal therapeutic system manufactured from a polymer in the form of an intravaginal device for delivering a beneficial drug to a vagina over a prolonged period of time.

BACKGROUND OF THE INVENTION

Vaginal devices for delivering a drug are known to the prior art. For example, U.S. Pat. No. 3,545,439 issued to Gordon W. Ducan discloses an intravaginal ring-shaped device that can be made of varying types of polymeric materials. The device is formed of a solid polymer containing drug that is released by diffusion to the vagina. The device optionally contains a tension spring for keeping it in the vagina. In U.S. Pat. No. 3,920,805 patentee Theodore J. Roseman discloses a solid, polymeric device that has a nonmedicated central solid core and an encircling medicated coating of the polymer. The device releases drug by diffusion and in a preferred embodiment, the device is ring-shaped with a flat tensioning spring molded in the nonmedicated central core.

While, the above-described devices are useful for certain applications, there are disadvantages frequently associated with these devices that limit their use. For example, generally the polymers used by the prior art are limited to thermoset polymers which often limits the amount of drug that can be loaded into the polymer and released by the polymer over time. Those versed in the art will recognize that if vaginal devices can be provided made of materials that are essentially-free from the above tribulations, such devices would be a valuable advancement in the art and a useful improvement.

OBJECTS OF THE INVENTION

Accordingly, it is an immediate object of this invention to provide an improved intravaginal delivery system for the controlled and continuous delivery of a drug over a prolonged period of time.

Yet another object of the invention is to provide an intravaginal system comprising materials easy to fabricate into systems and which materials can release drugs at meaningful rates over a prolonged period of time.

Yet still another object of the invention is to provide an intravaginal delivery system that is flexible, can have high drug loading, and which system can deliver drugs at a controlled and useful rate over a prolonged period of time.

Another object of the invention is to provide an intravaginal delivery system manufactured with vaginally compatible materials for releasing drugs over a prolonged period of time.

Other objects, features, aspects, and advantages of the invention will be more apparent to those versed in the art from the following detailed specification, taken in conjunction with the accompanying claims.

SUMMARY OF THE INVENTION

This invention concerns an intravaginal device useful for delivering drugs. The device comprises a wall made of a non-toxic thermoplastic polymer, or a non-toxic microporous polymer, which polymer in either instance, surrounds a reservoir containing an inner mass transfer conductor and a drug. The wall and the conductor are permeable to the passage of the drug by diffusion, but the permeability of the wall to the passage of drug is lower than through the conductor. Since the permeability through the wall is lower, passage through the wall is the rate determining step for releasing an effective amount of drug from the device to the vagina.

BRIEF DESCRIPTION OF THE DRAWINGS

In the drawings, which are not drawn to scale, but are set forth to illustrate various embodiments of the invention, the figures are as follows.

DETAILED DESCRIPTION OF THE DRAWINGS

Figure 1:
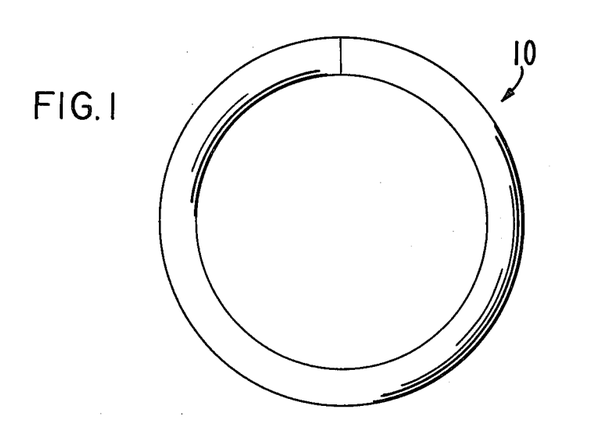
FIG. 1 illustrates an intravaginal system sized, shaped, and adapted for insertion and retention in a vagina.

Turning now to the drawings in detail, which are examples of intravaginal systems that can be used for releasing a drug to the vagina for the management of health and disease, and which examples are not to be construed as limiting the invention, one embodiment thereof is seen in FIG. 1 and identified by the numeral 10. The phase "intravaginal delivery system" as used herein refers to a controlled dosage form which provides preprogrammed, unattended delivery of drug, and for a time period, established to meet a specific therapeutic and beneficial need.

Figure 2:
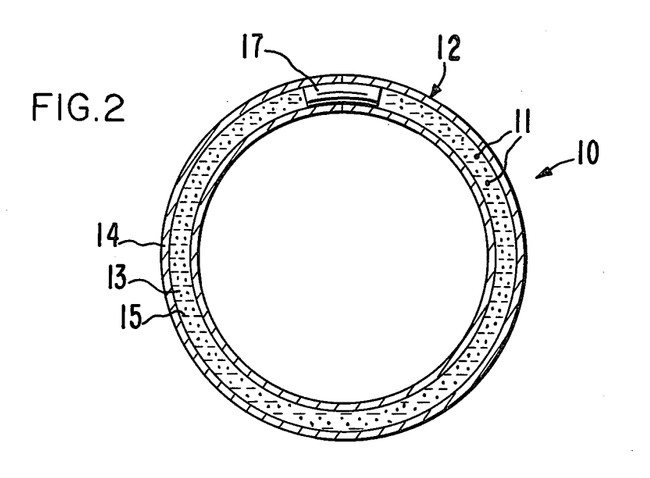
FIG. 2 illustrates the intravaginal system of FIG. 1 as seen in a cross-section, opened view and manufactured with means for forming a unit device and an internal reservoir.

System 10, as seen in FIG. 2, comprises a drug 11, selected for producing a desired physiologic or pharmacologic effect when delivered to the target receptor site, the vagina, and a delivery module 12. Delivery module 12 is essentially the body of system 10 and it comprises (a) a reservoir 13 for storing an amount of drug 11 required for execution of the prescribed therapeutic program, (b) a rate controller 14, or wall formed of a thermoplastic polymer or microporous polymer that maintains the prescribed rate of drug administered throughout the life of system 10, (c) an energy source 11, or the concentration of drug 11 in reservoir 13 that provides the driving means for transferring drug 11 from a higher amount in reservoir 13 to rate controller 14, (d) an inner mass transfer conductor 15 for housing drug 11 in reservoir 13, (e) a portal 14, which in this invention is a rate controller 14 that provides for the exit of drug 11 from module 12 to the vagina, and (f) a coupling member 17 made for uniting the module into a single annular shaped system. In FIG. 2, coupling member 17 is a solid material placed inside the module to form an end-to-end fluid-tight connection, for successful use of system 10 during release of drug 11.

Figure 3:
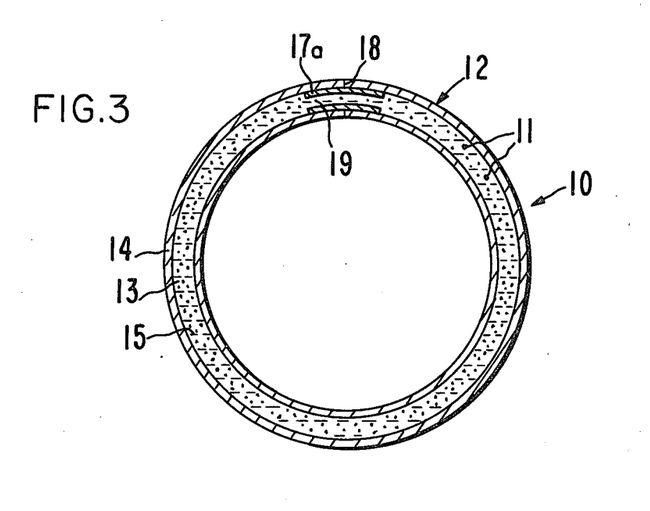
FIG. 3 depicts the vaginal system of FIG. 1 in opened view made with a means for forming an integral system which means is a different embodiment than the means illustrated in FIG. 2.

FIG. 3 illustrates a vaginal system 10 that is similar to the system illustrated in FIG. 2, with all the numbers as described in FIG. 2, except for the numbers discussed immediately below. In FIG. 3, number 17a represents a coupling member used as a joint for joining the ends, represented by a single line 18, of system 10 into an end-to-end essentially fluid impervious joint. Coupling 17a, in this embodiment, has a passageway 19 therethrough that permits the passage of a liquid mass transfer conductor 15 to flow in reservoir 13. In both embodiments, 17 and 17a, the coupling member is in mated relation with the inside of module 12 to form an essentially liquid-tight-union.

System 10, in the above Figures, comprises drug 11 stored in module 12 which module 12, is integrated into a unit sized, shaped, structured and adapted as a platform for placing in the vagina, can embrace many shapes. That is, the platform can have various continuous, curved shapes. Mainly, system 10 embraces a presently preferred single annular shape, which annular shape includes ring, oval, ellipse, toroidal, and like appearing annular shapes. The novel system 10 can be used for delivering drugs 11 to animals, warm-blooded mammals including humans and primates, farm animals and laboratory animals. The dimensions of the system will vary depending on the host and the shape used for delivering the drug. For example, at its maximum dimension the device will measure from one loci on the wall to a distant loci on the wall of from 0.4 cm to 16 cm, with presently preferred devices exemplified by an annular shaped system which can have an external diameter of from 0.5 cm to 14 cm, with general dimensions for various hosts as follows: humans 6 cm to 12 cm, sheep 2 cm to 7 cm, dogs 0.5 cm to 5.0 cm, swine 2 cm to 7.5 cm, household cats 0.4 cm to 4 cm, and dairy cattle 5 cm to 12 cm.

DETAILED DESCRIPTION OF THE INVENTION

In accordance with the practice of this invention, it has now been unexpectedly found that certain vaginally acceptable thermoplastic polymeric materials or microporous polymeric materials can be used for forming rate controller 14 of intravaginal system 10 for the controlled release of drug 11, for example by diffusion. The use of these materials is unexpected because these materials can be successfully used substantially free of any adverse affects on the vagina. The vagina is lined with an extremely delicate tissue, and it is essential, therefore, that materials forming system 10 do not adversely effect the vagina. The thermoplastic materials and the microporous materials used for the purpose of this invention are the vaginally compatible materials set forth below. By compatible is meant the materials are pharmaceutically acceptable within the environment of the vagina and generically to the host. That is, these materials do not break down in the vagina, there is no absorption of the materials, there is no deleterious action on the sensitive tissues in the area of placement and retention of the system over a prolonged period of time, and the materials do not harm drugs and carriers housed in system 10.

The thermoplastic polymers suitable for the purpose of this invention include polymers, copolymers and the like, that are capable of being softened by heating and hardened by cooling through a temperature range characteristic of the polymer, its crystalline melting or glass transition temperature, and in the softened state they can be shaped by flow into systems by molding or extrusion. The change for these materials upon heating is substantially physical. One example of a thermoplastic polymer that can be used for the present purpose is styrene-butadiene block copolymer. The styrene-butadiene block copolymer useful for manufacturing rate controller 14 includes those generally formed by initiation at a chain end of an already formed polymeric chain. The block copolymers are thermoplastic elastomers because of their ability to become fluid and moldable at elevated temperatures. These properties lend themselves to the manufacture of system 10. Generally, the styrene block copolymer will have a molecular weight in the range of 10,000 to 20,000 and the butadiene will have a molecular weight in the range of 40,000 to 100,000. The styrene butadiene block copolymers suitable for the present purpose are permeable to drugs, including antifertility agents such as, effective amounts of progestational and estrogenic vaginally-administered steroids.

Additional thermoplastic polymers that can be used for manufacturing system 10 include poly(methylacrylate), poly(butylmethacrylate), plasticized poly(vinylchloride), plasticized nylon, plasticized soft nylon, plasticized poly(ethylene terephthalate), poly(ethylene), poly(acrylonitrile), poly(trifluorochloroethylene), poly(4,4'-isopropylene diphenylene carbonate), poly(ethylene-vinyl esters), poly(ethylene-vinyl acetate), poly(vinyl chloride-diethyl fumarate), poly(esters of acrylic and methacrylic), partially hydrolyzed poly(vinyl acetate), poly(vinyl butyral), poly(amides), poly(vinyl carbonate), poly(urethane), poly(olefins), and the like. These polymers and their physical properties are known to the art and they can be synthesized according to the procedures disclosed in *Encyclopedia of Polymer Science and Technology*, Vol. 15, pages 508 to 530, 1971, published by Interscience Publishers, Inc., New York; *Polymers*, Vol. 17, 938 to 956, 1976; *Technical Bulletin* SCR-159, 1965, Shell Corp., New York; and references cited therein.

The vaginal drug delivery devices as provided herein, can be manufactured from porous and microporous tubing made from thermoplastic polymers that can be melt extruded to form a tubing structure. In one process, a tube is produced from an extrudable thermoplastic polymeric composition, by extruding with a commercial extruder through a die, a thermoplastic polymer that includes a leachable additive of prepore forming size. Typical examples of leachable components are water soluble modified starches, and other water soluble polymers such as polyethylene oxides, polyvinyl alcohol, sodium alignate, gelatin, hydroxyethyl cellulose, urea, and the like. The tube after extrusion is subjected to a liquid which leaches the leachable additive resulting in a porous tube.

In another process a thermoplastic polymer and a leachable sintered powder are mixed and extruded through a die of known shape and dimensions. A representative sintered powder is prepared by blending for example, hydroxypropyl cellulose and polyethylene glycol, followed by sintering the blend in a high speed mixture at an elevated temperature. Next a thermoplastic polymer and the powder are ground in a conventional grinder to a known sieve size. The blend is then extruded, and after extrusion the tube is subjected to intensive leaching or washing to produce a microporous structure in the tube wall. Another process for forming a porous tube comprises extruding in an extruder of a conventional type, and operated at a pressure needed for extrusion, a thermoplastic polymer and a blowing agent. Typical agents that create a foamed or a porous cellular structure include aryl-bis-sulfo-hydrazide, azodicarbonamide, azobisiso-butyronitrile, ammonium sesquicarbonate, and the like. The blowing agent releases gas and expands when the tube is exposed to a heat zone, which physical action and evolution of gas forms the porous structure. Procedures, equipment and materials suitable for manufacturing porous and microporous structures are known to the art in U.S. Pat. No. 3,223,761 issued to Raley; in U.S. Pat. No. 3,551,538 issued to Yamamoto et al; in U.S. Pat. No. 3,552,658 issued to Thomas; in U.S. Pat. No. 3,911,072 to Saito et al; and in U.S. Pat. No. 4,182,582 to Youval et al.

The microporous polymeric material can further be described as having pores that can be characterized as continuous pores interconnected through tortuous paths of regular and irregular shape. Generally, the final microporous materials can possess from 5 to 95% with a pore size which permits controlled release of the drug. Generally a pore size of from 10 angstroms to 200 microns, or more can be used for releasing the drug, with the micropores filling with a carrier through which the drug migrates to the exterior of the device. Materials useful for making microporous tubing includes the thermoplastic polymers described above and polymers such as polycarbonates, polyhexamethylene adipamide, polyolefins, polyalkylene sulfide, polyethers, polyesters, and like microporous homopolymers, copolymers and terpolymers.

Exemplary inner mass transfer conductors 15, include carriers that are suitable of housing drug 11 in reservoier 13, including liquid, semi-liquid carriers such as emulsions, gels, glycols, and the like. These carriers are permeable to the passage of drugs, they are capable of containing dissolved and undissolved drugs, and they are capable of forming a liquid carrier wall interface at the inner surface of wall 14. Typical carriers include a member selected from the group consisting of mineral, animal, fruit, nut, plant, sylvan, inorganic and organic oils. The carriers also include a member selected from the group consisting essentially of liquids, glycols, alkylene glycols, dialkylene glycols, poly(alkylene glycols), poly(oxyalkylene)-poly(oxyalkylene) copolymer, aqueous gels, and the like. The carriers also include aqueous carriers such as water, saline, and buffers. Representative of carriers include vegetable oil, marine oil, aqueous media such as water mixed with poly(alkylene glycols) including poly(ethylene glycols) having a molecular weight of 400 to 6000, poly(propylene glycol) having a molecular weight of 500 to 2000, glycerol polysorbate 80, and the like. Examples of carriers are known to the art in *Pharmaceutical Sciences*, by Remington, 1970, published by Mack Publishing Company, Easton, Penna.

The term drug as used herein includes any physiologically or pharmacologically active substances that produces a local or systemic effect when released in a biological environment, the vagina. The active drug can be inorganic, or organic compounds including drugs that act on the nervous system, drugs that act on tissues, muscles and organs, analgesics, anti-inflammatory, prostaglandins, anti-microbial, anti-viral, anti-fungal, spermicides, hormones, and the like. The beneficial drugs and their conventional doses are known in *Remington's Pharmaceutical* Sciences, 14th Edition, 1970, published by Mack Publishing Company, Easton, Penna.; and in *The Pharmacological Basis of Therapeutics*, by Goodman and Gilman, 4th Edition, 1970, published by MacMillian Company, London.

The terms spermicide and spermicidal as used herein are intended to encompass agents that kill sperm, as well as those agents which immobilize or render sperm ineffective for their intended effect by their spermicide semen contact. In one embodiment the spermicides include anionic surface active spermicides, non-ionic surface active spermicides and cationic surface active spermicides, and mixtures thereof. Exemplary spermicides that can be released by the vaginal device are represented by the following: di-isobutyl-phenoxypolyethoxy ethanol, dodecaethylene glycol monolaurate p-methanylphenyl polyoxyethylene, methoxypolyoxyethylene glycol laurate, nonylphenoxy-polyethoxy ethanol, polyethylene glycol of monoisooctyl phenol ether, polyoxyethylenenonyl phenol, polyoxyethylene nonylphenol ether, aminopropanesulfonate, nonylphenol nonaethoxylate, tri-isopropyl-phenoxypolyethoxy ethanol, sodium lauryl sulfate, glyceryl monoricinolate, spermicidal mixtures such as methoxypolyethylene glycol laurate and nonylphenoxypolyethoxyethanol, trioxymethylene and nonylphenoxypolyoxyethylene ethanol, p-triisopropyl-phenoxypolyethoxyethanol and sodium lauryl sulfate, p-diisobutylphenoxypolyethoxyethanol and nonylphenoxypolyethoxyethanol, sodium sulfodioctyl succinate and triisopropylphenyloxypolyethoxyethanol, glyceryl monoricinoleate and triisopropylphenyloxypolyethoxyethanol, and the like. The amount of spermicide in the vaginal device can be up to 100%. The amount of spermicide in the device, when the spermicide is mixed with a mass transfer conductor is about 0.5% to 80% by weight of the total ingredients in the vaginal device. The device, when in operation, releases a spermicidally effective amount of the spermicide over time, and more particularly from 50 microns to 500 milligrams per hour, or higher. The device releasing the spermicide can be positioned prior to intercourse in the vagina, and removed in a period of time after intercourse, or the device can be inserted and maintained in the vagina for several days up to a month.

The vaginal device also can be used for estrogen replacement therapy, as related to ovarian functions. The cessation of ovarian function during middle life is a physiological event. It is medically accepted this event is the basis of the menopausal period. The menopausal period does not happen all at once, and this critical period of life that occurs in women is often referred to as the climacteric. The menopausal period is characterized by menopausal symptoms initiated by a decrease is estrogen secretion, which follows the cessation of cyclical ovulation and menstruation. The menopausal symptoms generally include hot flashes, fatigue, insomnia, obesity, wrinkles and emotional lability, and the postmenopausal osteoporosis or bone deterioration. It is generally recognized estrogen therapy, and estrogen in conjunction with progestin therapies, are useful for the management of the climacteric. The vaginal device provided by the invention make available a method useful for relieving or preventing menopausal, perimenopausal, and postmenopausal symptoms. Exemplary estrogens useful for controlling the symptons include estradiol, estradiol benzoate, estradiol cypionate, estradiol dipropionate, estradiol enanthate, conjugated estrogen, estriol, estrone, estrone sulfate, ethinyl estradiol, estrofurate, quinestrol, and mestranol. The amount of naturally occurring or synthetic estrogen in a device is from 5 milligrams to 2,500 milligrams or more, and it is released at a rate of 1 microgram to 7 milligrams per hour, per day, or longer.

The vaginal device also can be used for the control of ovulation, or the prevention of pregnancy by suppressing ovulation, by administering contraceptive hormones. The contraceptive hormones useful for this purpose include progestational and estrogenic hormones. These hormones when released into the vagina are absorbed into the body and are thought to prevent conception by inhibiting the release of luteinizing hormone-releasing factor from the hypothalmus. This physiological action prevents the follicle stimulating hormone from stimulating an ovarian follicle to grow, and it also prevents the luteinizing hormone from triggering ovulation.

The contraceptive hormones that are used for the program of the invention include broadly antifertility steroids that can be used for regulating the fertility or ovulatory cycle in females of reproduction age. The contraceptive hormones include progestational and estrogenic steroids. The term progestational steroid as used herein embraces progestogen, which term is used in the pharmaceutical art to generically describe steroids possessing progestational activity. The progestational steroids further include naturally occurring steroids and synthetic steroids known as progestins. Exemplary progestational steroids include progesterone or preg-4-ene-3,20-dione; 17α-hydroxy-progesterone or 17α-hydroxypregn-4-ene-3,20-dione; 17α-hydroxyprogesterone 3-cyclopentyl enol; medrogestone or 6,17-dimethylpregna-4,6-diene-3,20-dione; medroxyprogesterone or 17α-hydroxy-6α-methylpregn-4-ene-3,-20-dione; megestrol acetate or 17α-hydroxy-6 methylpregna-4,6-diene-3,20-dione; chlormadione acetate or 6-chloro-17-α-hydroxypregna-4,6-diene-3,20-dione acetate; allylestrenol or 17-(2-propenyl)ester-4-en-17β-ol; ethynodiol or 19-nor-17α-pregn-4-en-20-yne-3β,17β-diol; ethynodiol diacetate; lynestrenol or 19-nor-17α-pregn-4-en-20-yn-17-ol; norethindrone or 17-hydroxy-19-nor-17α-pregn-4-en-20-yn-3-one; norethynodrel or 17-hydroxy-19-nor-17α-pregn-5(10)-en-20-yn-3-one; norgestrel or 13-ethyl-17-hydroxy-18,19-dinor-17α-pregn-4-en-20-yn-3-one; norgesterone or 17-hydroxy-19-nor-17α-pregna-5(10), 20-dien-3-one; quingestrone or progesterone cyclopentyl-3-enol ether; and other progestins such as norvinesterone; oxogestone and tigestol. The estrogenic hormones used for controlling the ovulatory cycle include estradiol or estra-1,3,5(10)-triene-3,17β-diol; estradiol 3-benzoate; estradiol 3-acetate; estradiol 3,17-diacetate; estriol or estra-1,3,5,(10)-triene-3,16α-17β-triol; estrone or 3-hydroxy-estral-1,3,5-(10)-trien-17-one; ethinyl estradiol or 19-nor-17α-pregna-1,3,5(10)-trien-20-yne-3,17-diol; mestranol or 3-methoxy-19-nor-17α-pregna-1,3,5(10)-triene-20-yn-17-ol; quinestradiol or 3-(cyclopentyloxy)-estra-1,3,5(10)-trien-16α-diol; quinestrol or 3-(cyclopentyloxy)-19-nor-17α-pregna-1,3,5(10)-trien-20-yn-17-ol; and other estrogens, such as estrazinol; and estrofurate.

The administration of a contraceptive hormone, or the administration of a combination of contraceptive hormones in the vagina for entry into the systemic circulation, which act primarily through the mechanism of gonadotropin suppression due to the progestational and the estrogenic activities of the steroids, with the resulting inhibition of ovulation, can be effected by the programs provided by the invention. One program for administering the naturally occurring steroid progesterone to the vagina can be generically described as three-weeks-on and one-week off program. The program comprises the steps of (1) inserting a delivery device into the vagina on the fifth day of the menstrual cycle, counting the first day of bleeding as day one, (2) retaining the system in the vagina for 20 to 21 days, preferably for three weeks, (3) administering from 1 microgram to 500 micrograms of progesterone to the vagina daily, preferrably into the vaginal fluid during the three week period, (4) removing the system from the vagina for one week, with no progesterone delivered during this period, and (5) repeating the contraceptive program at the end of this latter period by inserting a new delivery system into the vagina.

Another contraceptive program that can be used for the management of the ovulatory cycle comprises delivering progesterone to the vagina for one week from the fifth day to the twelfth day of the intermenstrual period. The system is positioned in the vagina beginning with day five of the menstrual period, counting the first day of bleeding as day one.

The contraceptive programs for delivering progestins to the vagina comprise delivering the hormonal steriod to the vagina preferrably to the vaginal mucosa, at the rate of 1 microgram to 2500 micrograms a day. The contraceptive programs presently preferred are the three-weeks-on and one-week-off, and the fifth to the twelfth day intermenstrual period programs as described above. The progestins include norethindrone, norethynodrel, norgestrel, and the like.

The contraceptive programs provided by the invention also include delivering a combination of a progestational and an estrogenic steroid to the vaginal environment. The program comprises inserting vaginal delivery system in the vagina that releases from 0.1 microgram to 3000 micrograms each at a continuous rate for three weeks of the four week cycle, or by using a program that corresponds to the oscillatory pattern exhibited by the normal ovarian cycle. Representative combinations that can be simultaneously released from the system include natural estrogen and natural progesterone; 35 mcg/day of ethinyl estradiol and 0.5 mg/day of norethindrone; 50 mcg/day of ethinyl estradiol and 1.0 mg/day of ethynodiol diacetate; 75 mcg/day of mestranol and 5.0 mg/day or norethyndrel; 30 mcg/day of ethinyl estradiol and 0.3 mg of norgestrel; 50 mcg/day of ethinyl estradiol and 0.5 mg of norethindrone; 80 mcg/day of mestranol and 1.0 mg of norethindrone; 50 mcg/day estrogen and 0.1 mg/day of progesterone; 100 mcg/day or estrogen and 0.4 mg/day or norethindrone; 40 mcg/day or estrogen and 0.5 mg/day of norgestrel; and the like. The vaginal system houses from about 2 mcg of 5 grams of estrogenic steroid and about 2 mg to 5 grams of progestational steroid alone or in combination. The abbreviation mcg indicates microgram and mg indicates milligram, and/day indicates the rate of delivery per day. Generally, the progestational or the estrogenic contraceptive steroid will be released at the rate or 0.05 micrograms to 50 milligrams per day, excluding the specific contraceptive programs set fourth above.

Additionally, the above progestational and estrogenic agents can be in the form of their pharmacologically accepted derivatives, such as their hydroxy or keto groups can be in a derivative form for the present purpose. The progestational or estorgenic derivative used should easily convert to the parent agent upon its release from the device by biological activities such as enzymatic transformation, pH assisted hydrolysis in the vagina, tissue and metabolism and the like. The derivative can also be used to control the solubility of the agent in the liquid core and to assist in metering the agent from the device. Suitable derivatives include without limitation, esters with pharmaceutically acceptable acids such as acetate, glucuronate, benzoate, propionate, butyrate, valeroate, hexanoate, heptanoate, maleate, citrate, succinate, tartrate, fumarate, malate, ascorbate, sulphate, phosphate and the like; ethers such as lower alkoxy-tetrahydropyran-yl, unsubstituted tetrahydropyran-yl, silyl moieties, trifluoromethyloxy, cyclopentylenol ethers and other functional groups such as ureido, and the like.

The materials used for manufacturing the coupling member are generally physiologically inert materials. The coupling member can be made from the same material as the vaginal system, or the coupling member can be made from a different material than the materials used to make the vaginal device. The coupling member, when placed inside a tubular wall forming the system has the same shape as the system and it cooperates with the tube to form a single, annular device. The coupling generally has a diameter measured across its cross-section equivalent to the inside diameter of the tubular member forming the system. Typical materials for forming the coupling are those listed above. Also, the coupling can be made from a hydrophilic polymer, such as a sparingly to moderately cross-linked hydrogel that swells 5 to 20% when in place in the presence of a fluid carrier in the system. Representative hydrophilic polymers include polyglycolmethacrylate, copolymeric diethylene glycolmethacrylate and methylmethacrylate, polyacrylonitrite, polymethacrylamide, polyhydroxylathyl methacrylate, and the like.

The coupling used for joining the two ends can be held in firm, fluid tight relation by solvent bonding, or by adhesive attachment. When a solvent is used, the surfaces of the coupling, and the inside of the tube are moistened with an organic solvent that causes the surfaces to feel tacky, and when placed in contact the surfaces then bonds and adheres then into a fluid tight union. The ends of the member can be adhesively united to form a closed system by applying an adhesive substance to the surfaces that hold the ends together by surface attachment. For the above procedures, the solvent include organic solvents such as methylene chloride, ethylene dichloride, trichlorobenzene, dioxan, isophorone, tetrahydrofuran, aromatic and chlorinated hydrocarbons, mixed solvents, such as 50/50 ethylene dichloride/diacetone alcohol; 40/60 alcohol/toluene; 30/70 alcohol/carbon tetrachloride, and the like. Suitable adhesive include natural adhesives and synthetic adhesives, such as, animal, nitrocellulosic, polyamide, phenolic, amino, epoxy, isocyanate, acrylic, silicate, organic adhesives of polymers, and the like. The adhesives are known to the art in *The Encyclopedia of Chemistry,* Second Edition, edited by George L. Clark and Gessner G. Hawley, 1966, published by VanNostrand Reinhold Co., Cincinnati, Ohio; and the solvents are known in *Encyclopedia of Chemical Technology,* Kirk-Othmer, Sec. Ed., Vol. 16, 1969, published by Interscience, Publishers Inc., New York.

The following examples are merely illustrative of the present invention and they should not be considered as limiting the scope of the invention in any way, as these examples and equivalents thereof will become apparent to those versed in the art in the light of the present disclosure, the drawings and the accompanying claims.

EXAMPLE 1

Figure 4:
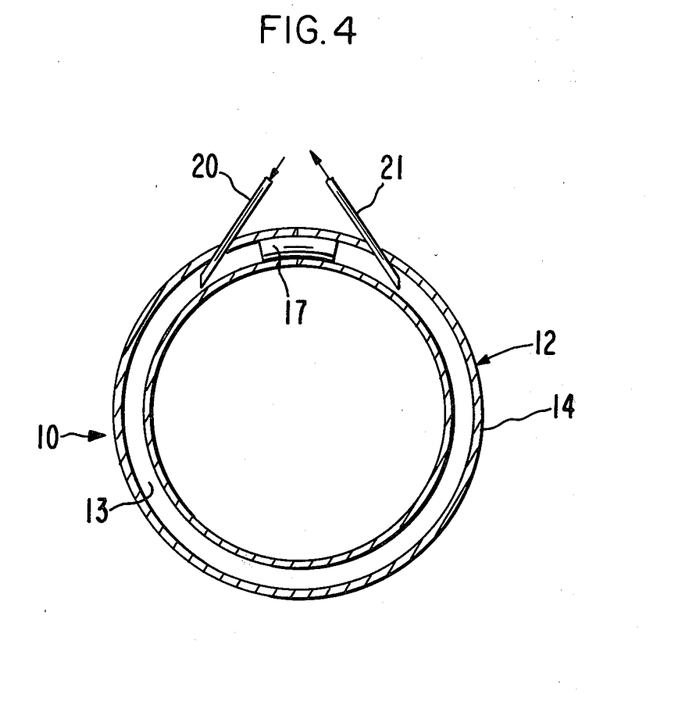
FIG. 4 illustrates the vaginal system of FIGS. 1 to 3 in opened section showing means for filling the system.

Intravaginal systems used for the purpose of this invention were manufactured as follows: First, a section of the styrene butadiene block copolymer vaginal acceptable tubing was washed with water for 48 to 56 hours, and then dried in air at room temperature. Then, the tubing was cut into appropriate lengths and shaped like a ring, as seen in FIG. 4, and molded into a torus at 165° C. Next, a solid polymeric plug 17, made of the copolymer, and having an utside diameter equivalent to the inside diameter of the tube was very lightly dampened with methylene chloride and inserted into the tube for joining the opened tube at its two ends, thereby forming a closed system. Then the hollow ring was filled by injecting a steroid carrier mixture into reservoir 13 through inlet port or needle 20 with continuous filling of reservoir 13 until all the air is displaced through outlet port or needle 21. This procedure completely fills reservoir 13. Finally, the needle punctures were sealed with a little methylene chloride. Reservoir 13 was filled with progesterone in polyethylene glycol having a molecular weight of 400, 5% wt/wt.

EXAMPLE 2

Following the general procedure of Example 1, additional systems 10 were prepared having a toroidal shape and made with the same copolymer. The systems were manufactured with an internal placed coupling in mated relation with the inside of the tube to form a single toroidal system. The systems were made with a wall 14 having a thickness of 1.78±0.08 mm, an internal diameter of 6 mm, and outside diameter of 4.4 cms, and a reservoir containing 35% progesterone and 65% polyethylene glycol having a molecular weight of 600.

EXAMPLE 3

The procedure of Example 2 was repeated with conditions as described except the systems of this example had a toroidal shape with a wall thickness of 2.79±0.08 and the reservoir housed 50% progesterone and 50% polyethylene glycol having a molecular weight of 600. The other dimensions were as described previously.

EXAMPLES 4-5

The procedures of Examples 1 to 3 are repeated with the couplings or inserts made of poly(vinylchloride) with a passage therethrough, or of cross-linked poly(-glycolmethacrylate). The couplings 17 are positioned inside the tubular member and they extend from the ends of the member a distance therein that imparts both structural support and continuity to the manufactured closed, annular ring. The cooperation of the couplings with the member acting as a unit provides a system suitable for intimate anatomical contact and for beneficial drug release within a vagina.

EXAMPLE 6

A vaginal device useful for releasing a spermicide is manufactured as follows: first a microporous cellulose tube having a thickness when dry of 25 microns, and a thickness when wet of 50 microns is shaped like a ring. Then, a solid polymeric connector made of ethylene vinyl acetate copolymer having a vinyl acetate content of 45% is moistened with methylene chloride and inserted into the ends of the tube for joining the tube into a closed system comprising a microporous wall surrounding and defining a hollow reservoir. Next, the reservoir is filed by injecting into the reservoir nonylphenoxypolyethoxy ethanol, 30% by weight, in an aqueous carrier.

EXAMPLE 7

The procedure of Example 6 is repeated with the reservoir in this vaginal device changed with nonylphenoxypolyethoxy ethanol and polyoxyethylenenonyl phenol ether in aqueous carrier.

EXAMPLES 8–9

The procedure of Example 6 is followed for producing vaginal devices, which devices comprise, (1) a wall of microporous polyvinylchloride with the reservoir containing ethinyl estradiol and norethindrone in silicone oil; or (2) a wall of microporous polyhexamethylene adipamide with ethinyl estradiol and norethyndiol in castor oil in the reservoir.

The delivery of steroids at meaningful rates from three systems made according to the mode of the invention was measured from three toroidal shaped systems. The results were as follows: (1) a system having a styrene-butadiene copolymer wall thickness of 2.79±0.08 mm and a progesterone loading of 0.7 gr had a steady state of release rate of 5.63±0.24 mg per day; (2) a system having a styrene-butadiene copolymer wall thickness of 1.78±0.08 mm and a progesterone loading of 1.3 gr had a steady state release rate of 9.49±0.25mg per day; and (3) a system having a styrene-butadiene copolymer wall thickness of 0.75±0.08 mm and a norethindrone loading of 0.4 gr had a steady state release rate of 0.56±0.07 mg per day as measured over a prolonged period of 120 days.

Also, the systems containing the norethisterone were placed in the vagina of fertile women. The systems were comfortable and well-received by the vagina and the host. The systems are preferably placed between the rear endometrial wall of the vagina and the upper edge of the pubic bone. In this place, the medicating system releases a contraceptively effective amount of steroid over a prolonged period of 75 days to yield the intended effect.

It will be understood to those versed in the art in the light of the present specification, drawings and the accompanying claims that the invention makes available to the art both a novel and useful vaginal system for delivering drugs such as progestational and estrogenic steroids to produce a desired antifertility effect; and spermidices for their effects, the rate of release from these systems can be controlled to product this effect, while simultaneously overcoming the problems associated with the prior art. It will be further understood to those versed in the art that different embodiments of this invention can be made without departing from the spirit and the scope of the invention. Accordingly, it is to be understood the invention is not to be construed as limited, but embraces all equivalents inherent herein.

I claim:

1. A method for regulating the ovulatory cycle in a woman, which method comprises the steps of:
   a. positioning in the vagina of the woman a device for delivering a member selected from the group consisting of a progestational and estrogenic hormone, said device comprising:
      1. a wall formed of a non-toxic tube shaped polymeric material united at its ends by a coupling placed within the tube, which wall surrounds;
      2. an internal reservoir containing the hormone, and a carrier for the hormone; and
   b. delivering the hormone to the vagina at a preprogrammed, continuous and controlled rate from the device in an effective amount for regulating the ovulatory cycle.

2. The method for regulating the ovulatory cycle according to claim 1 wherein the coupling is a solid material.

3. The method for regulating the ovulatory cycle according to claim 1 wherein the coupling has a passageway therethrough.

4. The method for regulating the ovulatory cycle according to claim 1 wherein the device delivers the progestational hormone in an effective amount for 21 days for regulating the ovulatory cycle.

5. The method for regulating the ovulatory cycle according to claim 1 wherein the device delivers the progestational hormone and the device is placed in the vagina on the fifth day of the ovulatory cycle.

6. The method for regulating the ovulatory cycle according to claim 1 wherein the device delivers the progestational hormone, and the device is placed in the vagina on the fifth day of the ovulatory cycle counting the first day of menstrual bleeding as day one of the ovulatory cycle, and wherein the device is removed from the vagina for one week after three weeks in the vagina.

7. The method for regulating the ovulatory cycle according to claim 1, wherein the device delivers the progestational and estrogenic hormone in an effective amount for twenty-one days for regulating the ovulatory cycle.

8. The method for regulating the ovulatory cycle according to claim 1, wherein the device delivers the progestational and estrogenic hormones, and the device is placed in the vagina on the fifth day of the ovulatory cycle.

9. The method for regulating the ovulatory cycle according to claim 1 wherein the device delivers the progestational and estrogenic hormone, and the device is placed in the vagina on the fifth day of the ovulatory cycle counting the first day of menstrual bleeding as day one of the ovulatory cycle, and wherein the device is removed from the vagina for one week after three weeks in the vagina.

10. The method for regulating the ovulatory cycle according to claim 1, wherein the polymeric material is a thermoplastic.

11. The method for regulating the ovulatory cycle according to claim 1 wherein the polymeric material is microporous.

12. The method for regulating the ovulatory cycle according to claim 1 wherein the polymeric material releases the hormone by diffusion.

13. A method for delivering a spermicide to a vagina, which method comprises:
   a. placing in the vagina a device adapted, shaped and sized for easy placing and comfortable retention in the vagina, the device comprising:
      1. a wall formed of a non-toxic tube shaped polymeric material joined at its ends by a coupling placed within the tube, which wall surrounds;
      2. an internal reservoir containing a spermicide and a carrier for the spermicide; and,
   b. delivering the spermicide to the vagina at a preprogrammed, continuous and controlled rate from the device over time.

14. The method for delivering the spermicide to the vagina according to claim 13, wherein the coupling is a solid insert, and the spermicide is delivered in an effective amount for producing a spermicidal environment in the vagina.

15. The method for delivering the spermicide to the vagina according to claim 13, wherein the coupling has a passageway therethrough, and the spermicide is delivered in an effective amount for rendering ineffective sperm in the the vagina.

16. The method for delivering the spermicide to the vagina according to claim 13, wherein spermicide is a member selected from the group consisting of anionic, cationic and non-ionic surface active spermicides.

17. The method for delivering the spermicide to the vagina according to claim 13, wherein the spermicide is a member selected from the group consisting of di-isobutylphenoxypolyethoxy ethanol, dodecaethylene monolaurate, p-methanylphenyl polyoxyethylene ether, methoxypolyoxyethylene glycol laurate, nonylphenoxypolyethoxy ethanol, polyethyleneglycol monoisoctyl phenol ether, and polyoxyethylenenonyl phenol.

18. The method for delivering the spermicide to the vagina according to claim 13 wherein the polymeric material is a thermoplastic polymer.

19. The method for delivering the spermicide to the vagina according to claim 13 wherein the polymeric material is a microporous polymer.

20. The method for delivering the spermicide to the vagina according to claim 13 wherein the polymeric material releases the hormone by diffusion.

21. A method for relieving menopausal and postmenopausal symptoms in a woman, which method comprises:
   a. placing in the vagina of the woman a drug delivery device adapted, shaped and sized for easy placement and comfortable retention in the vagina, the device comprising:
      1. a wall formed if a non-toxic tube shaped polymeric material joined at its end, with the wall surrounding
      2. an internal reservoir containing a dosage amount of an estrogenic hormone and a carrier for the steroid; and
   b. delivering the estrogenic steroid to the vagina at a preprogrammed, continuous and controlled rate in a therapeutically effective amount for relieving the symptoms over time.

22. A method for managing estrogen replacement therapy in a woman, which method comprises the steps of:
   a. inserting in the vagina of a woman needing estrogen replacement, a vaginal drug delivery device adapted, shaped and sized for easy insertion and comfortable retention in the vagina, said device comprising:
      1. a wall formed of a non-toxic tube shaped polymeric material joined in a fluid tight relation at its end, with the wall surrounding and forming;
      2. an internal reservoir containing the estrogen steroid, and a carrier therefore; and
   b. delivering the estrogen from the device to the vagina in a continuous and controlled rate, and in a therapeutically effective amount useful for estrogen replacement therapy.

23. The method for managing estrogen replacement therapy in a woman according to claim 22 wherein the woman needing estrogen replacement is climacteric woman.

24. The method for managing estrogen replacement therapy in a woman according to claim 22 wherein the reservoir contains a dosage amount of the estrogen steroid for substantially performing the replacement therapy, and the estrogen steroid is a member selected from the group consisting of estradiol, estradiol benzoate, estradiol cypionate, estradiol dipropionate, estradiol enanthate, conjugated estrogen, estriol, estrone, estrone sulfate, ethinyl estradiol, estrofurate, estrogen, quinestrol and mestranol.

25. The method for managing estrogen replacement therapy in a woman according to claim 22 wherein the polymeric material is a thermoplastic polymer.

26. The method for managing estrogen replacement therapy in a woman according to claim 22 wherein the polymeric material is a microporous polymer.

27. The method for managing estrogen replacement therapy in a woman according to claim 22 wherein the device releases the steroid by diffusion.

28. A vaginal device adapted and sized for easy insertion and comfortable retention in a vagina, the device comprising: a shaped tube formed of microporous polymer and joined by a coupling inserted into the ends of the tube to form a device with an internal reservoir, said reservoir containing a drug and a carrier for the drug, which drug is released by the device at a controlled rate and in a therapeutically effective amount over a prolonged period of time.

29. The vaginal device adapted and sized for easy insertion and comfortable retention in the vagina according to claim 28, wherein the coupling has an outside diameter approximately equivalent to the inside diameter of the tube for essentially joining the tube ends in a liquid tight union.

30. The vaginal device adapted and sized for easy insertion and comfortable retention in the vagina according to claim 28 wherein the device has an annular shape and the coupling has a diameter approximately equivalent to the inside diameter of the tube for forming an essentially liquid imperivous union.

31. The vaginal device adapted and sized for easy insertion and comfortable retention in the vagina according to claim 28 wherein the coupling inserted into the tube is a solid polymer insert.

32. The vaginal device adapted and sized for easy insertion and comfortable retention in the vagina according to claim 28 wherein the coupling has a passageway therethrough for the carrier to flow in the reservoir.

33. The vaginal device adapted and sized for easy insertion and comfortable retention in the vagina according to claim 28 wherein the coupling is solvent bonded to the inside of the tube.

34. The vaginal device adapted and sized for easy insertion and comfortable retention in the vagina according to claim 28 wherein the coupling is adhesively joined to the inside of the tube.

35. The vaginal device adapted and sized for easy insertion and comfortable retention in the vagina according to claim 28 wherein the coupling is made from a hydrophilic polymer.

36. The vaginal device adapted and sized for easy insertion and comfortable retention in the vagina according to claim 28 wherein the carrier is a member selected from the group consisting of a liquid, water, saline, buffer, oil, emulsion and glycol.

37. The vaginal device adapted and sized for easy insertion and comfortable retention in the vagina according to claim 28 wherein the device is annular shaped and at its maximum dimensions measures from a loci on the curved tube to a loci on the distant curved tube of from 0.4 cm to 16 cm, and the coupling within the tube at its ends is in mated relation therewith to form an end to end liquidtight connection.

38. The vaginal device adapted and sized for easy insertion and comfortable retention in the vagina according to claim 28 wherein the tube comprises wall forming microporous polymer that is non-toxic and non-irritating to the vaginal tissues.

* * * * *